US011717593B2

(12) United States Patent
Carty

(10) Patent No.: US 11,717,593 B2
(45) Date of Patent: *Aug. 8, 2023

(54) IMPROVING ADHESIVE PROPERTIES

(71) Applicant: Avery Dennison Corporation, Glendale, CA (US)

(72) Inventor: Neal Carty, Mentor, OH (US)

(73) Assignee: Avery Dennison Corporation, Glendale, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/776,323

(22) PCT Filed: Mar. 13, 2014

(86) PCT No.: PCT/US2014/025167
§ 371 (c)(1),
(2) Date: Sep. 14, 2015

(87) PCT Pub. No.: WO2014/159798
PCT Pub. Date: Oct. 2, 2014

(65) Prior Publication Data
US 2016/0038629 A1 Feb. 11, 2016

Related U.S. Application Data

(60) Provisional application No. 61/778,606, filed on Mar. 13, 2013.

(51) Int. Cl.
| | | |
|---|---|---|
| *A61L 24/00* | (2006.01) | |
| *A61K 31/192* | (2006.01) | |
| *A61L 15/58* | (2006.01) | |
| *C09J 153/02* | (2006.01) | |
| *C09J 11/08* | (2006.01) | |
| *A61K 9/70* | (2006.01) | |
| *C08L 1/28* | (2006.01) | |
| *C08L 39/06* | (2006.01) | |
| *A61L 24/06* | (2006.01) | |
| *A61L 24/08* | (2006.01) | |

(52) U.S. Cl.
CPC ........ *A61L 24/0015* (2013.01); *A61K 9/7053* (2013.01); *A61K 31/192* (2013.01); *A61L 15/585* (2013.01); *A61L 24/001* (2013.01); *A61L 24/0094* (2013.01); *A61L 24/06* (2013.01); *A61L 24/08* (2013.01); *C08L 1/286* (2013.01); *C08L 39/06* (2013.01); *C09J 11/08* (2013.01); *C09J 153/02* (2013.01); *A61L 2300/21* (2013.01); *C08G 2170/20* (2013.01)

(58) Field of Classification Search
CPC ... A61K 9/7053; A61K 31/192; A61L 24/001; A61L 24/0094; A61L 15/585; A61L 24/08; A61L 24/06; A61L 24/0015; A61L 2300/21; C09J 11/08; C09J 153/02; C08L 1/286; C08L 39/06; C08G 2170/20
See application file for complete search history.

(56) References Cited

U.S. PATENT DOCUMENTS

| | | | |
|---|---|---|---|
| 4,194,995 A | | 3/1980 | Schermann et al. |
| 4,675,009 A | | 6/1987 | Hymes et al. |
| 4,806,359 A | | 2/1989 | Radebaugh et al. |
| 4,931,283 A | | 6/1990 | Tsuk |
| 5,116,621 A | | 5/1992 | Oji et al. |
| 5,141,961 A | | 8/1992 | Coapman |
| 5,236,713 A | | 8/1993 | Wato et al. |
| 5,273,757 A | * | 12/1993 | Jaeger .................. G01N 33/521 424/448 |
| 5,389,376 A | | 2/1995 | Duan et al. |
| 5,441,741 A | | 8/1995 | Cheong |
| 5,505,956 A | | 4/1996 | Kim et al. |
| 5,534,561 A | | 7/1996 | Volke |
| 5,536,263 A | | 7/1996 | Rolf et al. |
| 5,591,447 A | | 1/1997 | Jensen |
| 5,656,286 A | | 8/1997 | Miranda et al. |
| 5,676,968 A | | 10/1997 | Lipp et al. |
| 5,681,579 A | | 10/1997 | Freeman |
| 5,700,478 A | | 12/1997 | Biegajski et al. |

(Continued)

FOREIGN PATENT DOCUMENTS

| | | |
|---|---|---|
| CN | 1143318 | 2/1997 |
| CN | 101045041 | 10/2007 |

(Continued)

OTHER PUBLICATIONS

Mikhail M. Feldstein, et al., Relation of glass transition temperature to the hydrogen bonding degree and energy in poly(N-vinyl pyrrolidone)blends with hydroxyl-containing plasticiezers: 3. Analysis of two glass transition temperatures featured for PVP solutions in liquid poly(ethylene glycol), Polymer, 2003, 1819-1834, vol. 44.
International Search Report issued in corresponding IA No. PCT/US14/25167 dated Jul. 2, 2014.
Yakurigaku, 6th edition, p. 459, Nov. 20, 2012.
Search report issued in corresponding Chinese Application No. 201480019743.1 dated Jan. 17, 2018.
He et al., General Practitioner's Guidelines for Medication Use, Beijing Science and Technology Press, Nov. 30, 2010, 1205.

(Continued)

*Primary Examiner* — Doan T Phan

(57) ABSTRACT

Various adhesive compositions are described which may optionally comprise one or more active agents such as pharmaceutical agents. The incorporation of one or more absorbents in combination with one or more crystallization inhibitors improves adhesive characteristics of the compositions. Also described are related methods of improving adhesive characteristics of adhesive compositions with the use of a combination of absorbent and inhibitor. Also described are related methods of using the compositions and articles incorporating such compositions.

9 Claims, 2 Drawing Sheets

(56) References Cited

U.S. PATENT DOCUMENTS

| | | | |
|---|---|---|---|
| 5,741,510 A | 4/1998 | Rolf et al. | |
| 5,814,032 A | 9/1998 | Hori et al. | |
| 5,830,505 A | 11/1998 | Fisch et al. | |
| 5,891,957 A | 4/1999 | Hansen et al. | |
| 6,024,975 A | 2/2000 | D'Angelo et al. | |
| 6,024,976 A | 2/2000 | Miranda et al. | |
| 6,143,317 A | 11/2000 | Himmelsbach et al. | |
| 6,159,498 A | 12/2000 | Tapolsky et al. | |
| 6,280,765 B1 | 8/2001 | Gueret | |
| 6,303,700 B1 * | 10/2001 | Chen | A61L 15/585 424/448 |
| 6,361,790 B1 | 3/2002 | Rolf et al. | |
| 6,375,963 B1 | 4/2002 | Repka et al. | |
| 6,399,091 B1 | 6/2002 | Berthold et al. | |
| 6,506,404 B1 | 1/2003 | Mayan et al. | |
| 6,562,363 B1 | 5/2003 | Mantelle et al. | |
| 6,583,220 B1 * | 6/2003 | Lipman | C09J 153/02 525/54.3 |
| 6,585,997 B2 | 7/2003 | Moro et al. | |
| 6,616,642 B1 | 9/2003 | Jensen et al. | |
| 6,623,751 B2 | 9/2003 | Gueret | |
| 6,638,528 B1 | 10/2003 | Kanios | |
| 6,652,876 B2 | 11/2003 | Radloff et al. | |
| 6,676,962 B1 | 1/2004 | Muller | |
| 6,710,100 B1 * | 3/2004 | Lipman | A61L 15/585 428/497 |
| 6,740,711 B1 | 5/2004 | Lipman et al. | |
| 6,878,385 B2 | 4/2005 | Jensen et al. | |
| 6,964,987 B1 | 11/2005 | Auguste et al. | |
| 7,018,647 B1 | 3/2006 | Yamasaki et al. | |
| 7,063,859 B1 | 6/2006 | Kanios et al. | |
| 7,244,447 B2 | 7/2007 | Hsu et al. | |
| 7,256,234 B2 | 8/2007 | Nierle et al. | |
| 7,297,741 B2 * | 11/2007 | St. Clair | C08F 297/04 428/517 |
| 7,332,180 B2 | 2/2008 | Bracht | |
| 7,820,177 B2 | 10/2010 | Kruse et al. | |
| 7,829,099 B2 | 11/2010 | Woeller et al. | |
| 7,993,654 B2 | 8/2011 | Woeller et al. | |
| 2001/0031787 A1 | 10/2001 | Hsu et al. | |
| 2002/0004065 A1 * | 1/2002 | Kanios | A61K 9/7061 424/449 |
| 2002/0119185 A1 | 8/2002 | Radloff et al. | |
| 2002/0192273 A1 | 12/2002 | Buseman et al. | |
| 2003/0016868 A1 | 1/2003 | Oh et al. | |
| 2003/0077316 A1 | 4/2003 | Nichols et al. | |
| 2003/0082227 A1 | 5/2003 | Sournac et al. | |
| 2003/0109819 A1 | 6/2003 | Tsuruda et al. | |
| 2003/0133970 A1 | 7/2003 | Bracht et al. | |
| 2003/0016187 A1 | 8/2003 | Labtec | |
| 2003/0175328 A1 | 9/2003 | Shefer et al. | |
| 2003/0175333 A1 | 9/2003 | Shefer et al. | |
| 2003/0225356 A1 * | 12/2003 | Kulichikhin | A61L 15/585 602/54 |
| 2004/0018241 A1 * | 1/2004 | Houze | A61K 9/0014 424/486 |
| 2004/0101551 A1 | 5/2004 | Selzer | |
| 2004/0146548 A1 | 7/2004 | Takada et al. | |
| 2004/0151774 A1 | 8/2004 | Pauletti et al. | |
| 2004/0153040 A1 | 8/2004 | Martineau et al. | |
| 2004/0241215 A1 | 12/2004 | Lipman | |
| 2005/0048102 A1 | 3/2005 | Tapolsky et al. | |
| 2005/0074486 A1 | 4/2005 | Juel-Friis et al. | |
| 2005/0202073 A1 | 9/2005 | Jackson et al. | |
| 2005/0281860 A1 | 12/2005 | Fischell et al. | |
| 2005/0281869 A1 | 12/2005 | Kruse et al. | |
| 2006/0015007 A1 | 1/2006 | Aue et al. | |
| 2006/0029654 A1 | 2/2006 | Cassel | |
| 2006/0034904 A1 | 2/2006 | Weimann | |
| 2007/0051376 A1 | 3/2007 | Kulichikhin et al. | |
| 2007/0148216 A1 | 6/2007 | Yoshitake et al. | |
| 2007/0154527 A1 | 7/2007 | Myers et al. | |
| 2007/0179461 A1 * | 8/2007 | Sambasivam | A61L 15/58 604/336 |
| 2007/0255197 A1 | 11/2007 | Humberstone et al. | |
| 2007/0259029 A1 | 11/2007 | McEntire et al. | |
| 2007/0298089 A1 | 12/2007 | Saeki et al. | |
| 2008/0026040 A1 | 1/2008 | Farr et al. | |
| 2008/0102103 A1 | 5/2008 | Bevacqua et al. | |
| 2008/0292684 A1 | 11/2008 | Colombo et al. | |
| 2008/0311167 A1 | 12/2008 | Oronsky et al. | |
| 2008/0311178 A1 | 12/2008 | Ishikura et al. | |
| 2008/0311217 A1 | 12/2008 | Oronsky et al. | |
| 2009/0010998 A1 | 1/2009 | Marchitto et al. | |
| 2009/0041832 A1 | 2/2009 | Govil et al. | |
| 2009/0053285 A1 | 2/2009 | Ali et al. | |
| 2009/0053290 A1 | 2/2009 | Sand et al. | |
| 2009/0238860 A1 | 9/2009 | Saeki et al. | |
| 2009/0252782 A1 | 10/2009 | Choi et al. | |
| 2009/0264806 A1 | 10/2009 | Tamura et al. | |
| 2009/0291140 A1 | 11/2009 | Korey | |
| 2009/0317451 A1 | 12/2009 | Hauser | |
| 2010/0003308 A1 | 1/2010 | Tapolsky et al. | |
| 2010/0022614 A1 | 1/2010 | Kawamura et al. | |
| 2010/0055153 A1 | 3/2010 | Majmudar | |
| 2010/0068248 A1 | 3/2010 | Funakoshi et al. | |
| 2010/0093673 A1 | 4/2010 | Oronsky | |
| 2010/0203107 A1 | 8/2010 | Koo et al. | |
| 2010/0256174 A1 | 10/2010 | Yamaguchi et al. | |
| 2010/0272784 A1 | 10/2010 | Kantner et al. | |
| 2010/0311700 A1 | 12/2010 | Yoshitake et al. | |
| 2010/0322996 A1 * | 12/2010 | Wibaux | C09J 9/00 424/443 |
| 2011/0008413 A1 | 1/2011 | Qiu et al. | |
| 2011/0077608 A1 | 3/2011 | Macedo, Jr. | |
| 2011/0160194 A1 | 6/2011 | Inoo et al. | |
| 2011/0184328 A1 | 7/2011 | Chieze et al. | |
| 2011/0236465 A1 | 9/2011 | Hall et al. | |
| 2011/0306677 A1 | 12/2011 | Kataoka | |
| 2012/0029446 A1 | 2/2012 | Amano et al. | |
| 2012/0058175 A1 | 3/2012 | Amano et al. | |
| 2012/0064146 A1 | 3/2012 | Friis et al. | |
| 2012/0189686 A1 | 7/2012 | Houze et al. | |

FOREIGN PATENT DOCUMENTS

| | | |
|---|---|---|
| CN | 101147739 | 3/2008 |
| CN | 101574332 | 11/2009 |
| CN | 101780205 A | 7/2010 |
| CN | 102144991 | 8/2011 |
| EP | 0507160 A1 | 10/1992 |
| EP | 0728797 | 8/1996 |
| EP | 0764444 | 3/1997 |
| EP | 1547579 A1 | 6/2005 |
| EP | 2110125 | 10/2009 |
| JP | 1984-110616 | 6/1984 |
| JP | 1984-110617 | 6/1984 |
| JP | 1991-161436 | 7/1991 |
| JP | 2006-45099 | 2/2006 |
| KR | 10-2009-0110255 | 10/2009 |
| WO | 95/18603 | 7/1995 |
| WO | 02066087 A1 | 8/2002 |
| WO | 02/087645 | 11/2002 |
| WO | 2005/063215 | 7/2005 |
| WO | 2007/050580 | 5/2007 |
| WO | 2010/018559 | 2/2010 |
| WO | 2011/070318 | 6/2011 |

OTHER PUBLICATIONS

Search report issued in corresponding Chinese Application No. 201480019743.1 dated Feb. 5, 2018.

Saroha et al., "Transdermal Patch: A Discrete Dosage Form," International Journal of Current Pharmaceutical Research, 2011, vol. 3, Issue 3, pp. 98-108.

Matsumoto and Zografi. "Physical Properties of Solid Molecular Dispersions of Indomethacin with Poly(vinylpyrrolidone) and Poly(vinylpyrrolidone-co-vinylacetate) in Relation to Indomethacin Crystallization" Pharmaceutical Research 16, 1722-1728 (1999).

Jain and Banga. "Inhibition of crystallization in drug-in-adhesive type transdermal patches." International Journal of Pharmaceutics 394, 68-74 (2010).

(56) References Cited

OTHER PUBLICATIONS

Kim and Choi. "Effect of additives on the crystallization and the permeation of ketoprofen from adhesive matrix" International Journal of Pharmaceutics 236, 81-85 (2002).
International Preliminary Report on Patentability dated Sep. 15, 2015 issued in corresponding IA No. PCT/US2014/025167 filed Mar. 31, 2014.
Anonymous: "Issues in Pharmacology, Pharmacy, Drug Research and Drug Innovation", Jan. 9, 2012 (Jan. 9, 2012), ScholarlyEditions, USA.
Schulz: "Adsorption Properties of Crospovidone and Use of Crospovidone in Drug-In-Adhesive Patches", Freien Universitat Berlin, Mar. 2009 (Mar. 2009), pp. 32-40.
Pyka: "Lipophilicity Investigations of Ibuprofen", Journal of Liquid Chromatography and Related Technologies, vol. 32, No. 5, Feb. 9, 2009, pp. 723-731.

\* cited by examiner

IMPROVING ADHESIVE PROPERTIES

CROSS REFERENCES TO RELATED APPLICATIONS

The present application is a 371 of International Application No. PCT/US14/25167, which was published in English on Oct. 2, 2014, and claims the benefit of U.S. Provisional Patent Application No. 61/778,606 filed Mar. 13, 2013, both of which are incorporated herein by reference in their entireties.

FIELD

The present subject matter relates to improving adhesive properties. In certain versions, the subject matter relates to improving adhesive properties of adhesive compositions that release one or more active agents. The subject matter is particularly directed to medical adhesives containing one or more pharmaceutical active agents.

BACKGROUND

Adhesive compositions are known which introduce one or more active agents for release when placed in contact with human skin tissue. Vehicles or solvents are used to solubilize or suspend one or more active agents therein and to introduce the actives into the adhesive. Absorbents may be used in the compositions to absorb, retain, or transmit moisture or aqueous agents, which may be desirable in some compositions. Although satisfactory in certain respects, the combination of these components tends to inhibit and degrade the adhesive properties of the compositions.

It is also known to incorporate crystallization inhibitors in adhesive compositions that contain active agents. Without crystallization inhibitors, crystallization of the active agents contained in the adhesive may occur. This is undesirable because crystallization creates unpredictable variations in the rate of release of the actives and decreases the effectiveness of the actives. However, incorporation of such inhibitors in an active-containing adhesive typically requires additional agents that facilitate delivery of the active. The further combination of these components in an adhesive composition and particularly a pressure sensitive adhesive can detrimentally impact adhesive properties of the resulting composition.

Accordingly, a need exists for active-containing adhesive compositions that inhibit crystallization of the actives, exhibit improved and predictable release characteristics for the actives, provide improved solubility for the actives, absorb or retain moisture, and at the same time exhibit improved adhesive properties for the composition as a whole, and which can be readily tailored and utilized in a variety of different applications.

SUMMARY

The difficulties and drawbacks associated with previously known compositions are addressed by the compositions, articles, and related methods of the present subject matter as follows.

In one aspect, the present subject matter provides a method of enhancing adhesive properties of an adhesive composition, wherein the adhesive composition comprises an adhesive component, an absorbent, and a vehicle. The method comprises providing a crystallization inhibitor and incorporating the crystallization inhibitor in the adhesive composition in particular proportions to thereby enhance the adhesive properties of the resulting composition. As described in greater detail herein, incorporating the crystallization inhibitor into the composition improves adhesive properties of the composition such as tack and adhesion.

In another aspect, the present subject matter provides an adhesive composition comprising an adhesive component, a vehicle, an absorbent, and a crystallization inhibitor. In certain embodiments of the present subject matter, the components of the adhesive composition are incorporated in the composition at particular proportions relative to one another. The adhesive composition exhibits a Peel on polyethylene value of at least 0.5 N/in and a Tack of at least 10 N/in.

In yet another aspect, the present subject matter provides an article for adhesive attachment to a surface of interest. The article comprises a substrate defining at least one face. And, the article also comprises a region of an adhesive composition disposed on at least a portion of the face of the substrate. The adhesive composition includes (i) an adhesive component, (ii) a vehicle, (iii) an absorbent, and (iv) a crystallization inhibitor. The adhesive composition exhibits a Peel on polyethylene value of at least 0.5 N/in and a Tack of at least 10 N/in.

As will be realized, the subject matter is capable of other and different embodiments and its several details are capable of modifications in various respects, all without departing from the subject matter. Accordingly, the drawings and description are to be regarded as illustrative and not restrictive.

DETAILED DESCRIPTION OF THE EMBODIMENTS

Figure 1:
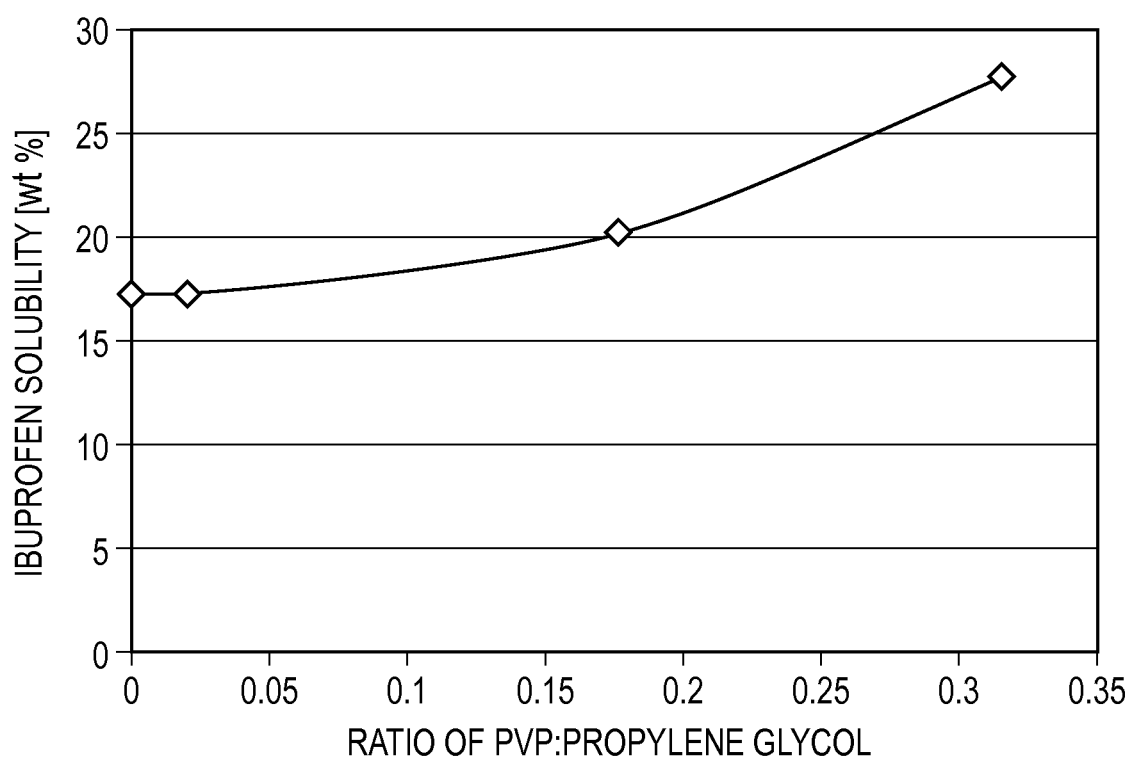
FIG. 1 is a graph of solubility of an active agent as a function of a ratio of two components in compositions according to the present subject matter.

The present subject matter is directed to enhancing adhesive properties of an active containing adhesive composition comprising a vehicle and one or more absorbents by incorporation of a crystallization inhibitor. More particularly, in certain versions, the subject matter is directed to improving adhesive properties such as tack and adhesion of pressure sensitive adhesives. The subject matter is generally directed to pressure sensitive adhesives but can encompass other types of adhesives. Although the present subject matter is primarily directed to adhesive compositions that contain one or more actives, it will be understood that the subject matter also encompasses adhesives which are free of actives. These and other aspects of the present subject matter are described in greater detail herein.

In many applications, it is desirable to incorporate a drug or other active agent(s) into an adhesive matrix to combine the therapeutic effects of the drug or active ingredient(s) with the adhesive. Often, one or more absorbents are incorporated into the adhesive to impart moisture transmission or absorption properties to the resulting composition. To deliver the active agents into the adhesive, a vehicle is used. The vehicle may also promote the delivery of the active agent to human skin tissue. In certain percentages, the combination of adhesive, vehicle, and active agent can result in a composition with inhibited or poor adhesive properties. As described herein, it has been discovered that incorporation of one or more crystallization inhibitors in an adhesive composition in particular proportions and/or in conjunction with certain other agents such as absorbents, improves adhesive properties of the drug-in-adhesive composition, while also improving the release and/or release characteristics the actives, active agents, drugs, and/or pharmaceuticals from the adhesive matrix to underlying skin.

Several aspects of the present subject matter, periodically referred to herein as a "drug-in-adhesive" system, include, but are not limited to the following. The active agents are controllably released from the adhesive composition into a receiving medium such as for example underlying biological tissue. The adhesive compositions having a crystallization inhibitor exhibit improved adhesive properties. When utilized in a blister treatment application, the adhesive compositions of the present subject matter have an ability to absorb fluid in the event that the blister has ruptured while also exhibiting good adhesive properties. The adhesive compositions exhibit good adhesive properties so that the compositions can remain on the skin for an extended period of time, for example 24 hours or more.

In certain embodiments, the present subject matter provides for inhibition of the crystallization of a drug within a hydrocolloid adhesive matrix in a composition that concurrently exhibits excellent adhesive properties. The composition used as the carrier, to solubilize the drug and deliver the drug into the adhesive matrix, generally comprises a polyhydric alcohol vehicle combined with at least one polyvinylpyrrolidone (PVP). Through the addition of the PVP to the polyhydric alcohol, crystallization of the active agent is inhibited. In certain versions of the present subject matter, the PVP increases the solubility of the drug in a polyhydric alcohol vehicle and the combination of polyhydric alcohol and PVP enhances the drug's release kinetics. At certain loadings, the incorporation of an absorbent into the compositions transforms the compositions from a non-tacky gel-like mixture into a functional pressure sensitive adhesive. The inclusion of the absorbent generally allows for higher loadings of the vehicle, crystallization inhibitor, and active agent into the adhesive, with a resulting composition exhibiting excellent adhesive properties.

When referring to adhesive properties that are improved by the inclusion of a crystallization inhibitor, the reference to adhesive properties includes one or more of: adhesion (force need to detach an adhesive sensitive to pressure from a substrate), release (force need to separate a self-adhesive from a liner), ability to adhere to a variety of substrates, cohesive strength (ability of adhesive molecules to remain connected to each other), tack (initial adhesion before pressure is applied or before the adhesive is allowed to contact a substrate for an extended period of time), viscosity, flexibility, elastic modulus, electric conductivity, flammability, glass transition temperature, green strength, hardness, ability to resist stress at the bond line, damping resistance (ability to resist deformation caused by vibration), cleavage strength (ability to resist forces that pull apart adhesive by separating two rigid surfaces bonded by the adhesive), peel strength, (ability to resist forces that pull apart adhesive by separating a flexible surface from a rigid surfaces bonded by the adhesive), creep (deformation of the adhesive due to application of a constant load), resistance to thermal expansion/contraction of the substrate, resistance to environmental temperature fluctuation, shrink (the reduction in volume over time), tensile strength, resistance to shock at a range of temperatures, ability to maintain adhesive performance despite exposure to UV light, moisture, salt, and other environmental conditions, migration (movement of the adhesive from the location of application on a facestock), ability to maintain tack after repeated removal and reapplication to a substrate, degree of surface preparation necessary for the adhesive composition to adhere to the substrate, initial bonding strength, force required for removal, long-term tackiness, ability to wet a substrate, chemical resistance. These adhesive properties are non-limiting examples of characteristics that may be improved by the inclusion of one or more crystallization inhibitors to an adhesive matrix that includes an adhesive, an absorbent, and a vehicle. The examples may include other properties, either similar to or different from those mentioned herein.

In certain versions of the present subject matter, compositions are provided which comprise (i) an adhesive as a continuous phase, (ii) an absorbent as a discontinuous phase dispersed in the continuous phase, and (iii) a crystallization inhibitor dissolved in a vehicle as a second discontinuous phase dispersed in the continuous phase. The compositions may optionally comprise one or more active agents. The vehicle is also used to deliver and release the active agent to underlying tissue when in contact with skin. The resulting adhesive compositions provide an improved drug-release feature without compromising absorption or adhesion performance. A representative example of an active agent is ibuprofen, though the subject matter is not limited to use solely with this active ingredient. Instead, as described in greater detail herein, a wide array of active agents or combinations of active agents can be incorporated in the present subject matter compositions.

The present subject matter provides a wide array of adhesive compositions which can be tailored to controllably release one or more active agent(s) from the adhesive composition, yet maintain adequate adhesive properties, and in many instances excellent adhesive properties. Table 1 set forth below lists representative adhesive compositions in accordance with the present subject matter. All percentages expressed herein are percentages by weight, unless noted otherwise.

TABLE 1

Adhesive Compositions

| Weight Percentage | Component |
|---|---|
| 20% to 90% | Adhesive |
| 0.1% to 50% | Absorbent |
| 0% to 20% | Active Agent(s) |
| 0.1% to 30% | Crystallization Inhibitor |
| 0.1% to 30% | Vehicle |

In one particular embodiment in accordance with the present subject matter, ibuprofen is dissolved in a mixture of PVP and propylene glycol and then incorporated into a styrene/isoprene hot-melt rubber adhesive matrix along with carboxymethycellulose absorbent. In many versions of the present subject matter, incorporating carboxymethylcellulose absorbent improves the adhesive properties of the composition.

Adhesive(s)

A wide array of adhesive components can be used in the adhesive compositions according to the present subject matter. Generally, the adhesive or adhesive component is a hot melt adhesive. In certain aspects, the present subject matter compositions comprise a hot melt pressure sensitive adhesive that is able to be processed at a temperature below 75° C. In some aspects the hot melt adhesive will soften at temperatures between about 60° C. and about 70° C. for low temperature processing so as to avoid the breakdown or degradation of active agents.

The adhesive matrix may be based on for example polyisobutylene, butyl rubber, polyacrylates, polyurethanes, silicone gum, natural gum rubber, SBR rubber or polyvinyl ether. Thermoplastic elastomers such as styrene-isoprene-styrene block copolymers and styrene-ethylene/propylene-styrene block copolymers may be used, and these may require optional tackifiers and plasticizers. Blends or mixtures of elastomers may be more easily employed.

Particularly suitable as bases for the pressure sensitive adhesives of the present subject matter are rubbers such as linear or radial A-B-A block copolymers or mixtures of these A-B-A block copolymers with simple A-B block copolymers. These block copolymers can be based on styrene-butadiene, styrene-isoprene, and hydrogenated styrene-diene copolymers such as styrene ethylene-butylene.

Suitable styrene-diene copolymers for the practice of the present subject matter are exemplified by a blend of linear styrene/isoprene/styrene triblock copolymer and linear styrene/isoprene diblock copolymer. Such a material is available from Shell Chemical as Kraton D-1161 and has a bound styrene content of about 15% and a diblock content of 17%. A second example is a blend of linear styrene/isoprene/styrene triblock copolymer and linear styrene/isoprene diblock copolymer available from Shell Chemical as Kraton D-1117 and which has a bound styrene content of about 17% and a diblock content of 33%.

An example of a suitable hydrogenated styrene-diene copolymer is a thermoplastic elastomer comprising a blend of clear linear triblock and diblock copolymer based on styrene and ethylene/butylene, with a bound styrene of 14% mass. Such a material is commercially available from Shell Chemical Company as Kraton G-1657. Another example is Kraton G-1652 from Shell Chemical Company, which is a thermoplastic elastomer comprised of a clear linear triblock copolymer based on styrene and ethylene-butylene, S-E/B-S, with a bound styrene content of about 30% by weight. Also suitable are polymers in which there is a combination of chemically saturated blocks and chemically unsaturated blocks. For example, a branched copolymer consisting of two polyisoprene chains attached to the rubber midblock of a styrene/ethylene-butylene/styrene triblock copolymer may be suitable. Such a material is available from Shell Chemical Company as Kraton Research Product RP6919. This material has a styrene content of 18%, an isoprene content of 36% and an ethylene-butylene content of 46% by weight. Also, a low styrene synthetic copolymer of butadiene and styrene, commonly called SBR rubber, can be used as a solid rubber.

Also particularly suitable are acrylic pressure sensitive adhesives, exemplified by an acrylic hot melt adhesive manufactured by Schenectedy Chemicals and having the designation Durotac 401. Another example is an acrylic solvent adhesive from Avery Chemicals called Polytex 7600.

Absorbent(s)

Similarly, a wide array of absorbents can be utilized in the adhesive compositions according to the present subject matter. Generally, the absorbent includes one or more hydrophilic polymers that are soluble or insoluble but swellable in water, as the moisture-absorbing component. Suitable insoluble swellable polymers include cross-linked sodium carboxymethyl cellulose, crystalline sodium carboxymethyl cellulose, cross-linked dextran and starch-acrylonitrile graft copolymer. The swellable polymer may also be a so-called "super absorbent" material such as starch sodium polyacrylate. Other hydratable polymers such as gluten and polymers of methyl vinyl ether and maleic acid and derivatives thereof may also be included. Suitable water soluble polymers include sodium carboxymethyl cellulose, pectin, gelatin, guar gum, locust bean gum, collagen, tragacanth gum, karaya gum starches, gum arabic, alginic acid and various sodium and/or calcium salts thereof. Other synthetic absorbents such as polyvinyl alcohol, polyvinyl acetate, polyvinyl pyrollidone, polyacrylic acid, polyhydroxyalkyl acrylates, polyacrylamides, high molecular weight polyethylene glycols and polypropylene glycols may be useful.

The super absorbent polymer (SAP), if used in the adhesive compositions, comprises a water-swellable, hydrogel-forming absorbent polymer capable of absorbing large quantities of liquids such as water, body fluids (e.g., urine, blood), and the like. Additionally, the SAP is capable of retaining such absorbed fluids under moderate pressures. Typically the SAP absorbs many times its own weight in water, preferably at least 50 times, more preferably at least 100 times, most preferably at least 150 times its weight in water. Additionally, the SAP exhibits good saline fluid absorption under load and high saline fluid absorption capacity. Typically the SAP absorbs at least 10 times, preferably at least 30 times, more preferably at least 50 times its weight in saline fluid. Even though the SAP is capable of absorbing many times its own weight in water and/or saline, it does not dissolve in these fluids.

The ability of the SAP to absorb water and/or saline fluid is related to the degree of crosslinking present in the SAP. Increasing the degree of crosslinking increases the SAP's total fluid holding capacity under load. The degree of crosslinking is preferably optimized to obtain a composition in which the rate and amount of absorbency are optimized. Useful SAPs are at least 10%, more preferably from about 10% to about 50%, and most preferably from about 20% to 40% crosslinked. Examples of suitable SAPs include crosslinked and polymerized $\alpha,\beta$-beta ethylenically unsaturated mono- and dicarboxylic acids and acid anhydride monomers including, e.g., acrylic acid, methacrylic acid, crotonic acid, maleic acid/anhydride, itaconic acid, fumaric acid, and combinations thereof.

Super absorbent polymers useful in the present subject matter include, e.g., crosslinked acrylate polymers, cross-linked products of vinyl alcohol-acrylate copolymers, cross-linked products of polyvinyl alcohols grafted with maleic anhydride, cross-linked products of acrylate-methacrylate copolymers, crosslinked saponification products of methyl acrylate-vinyl acetate copolymers, crosslinked products of starch acrylate graft copolymers, crosslinked saponification products of starch acrylonitrile graft copolymers, cross-linked products of carboxymethyl cellulose polymers and crosslinked products of isobutylene-maleic anhydride copolymers, and combinations thereof.

The super absorbent polymer(s) is typically in the form of particles and preferably are spherical and have an average particle size of from about 1 micrometer (μm) to about 400 (μm). Preferably the particles have an average particle size of from about 20 μm to about 200 μm, and more preferably from 20 μm to 150 μm. In one embodiment, the particle size of the particles is less than 150 μm, or less than 100 μm. Useful commercially available super absorbent particles include, e.g., sodium polyacrylate super absorbent particles available under the AQUA KEEP series of trade designations including, e.g., particles having an average particle size of from about 20 μm to about 30 μm available under the trade designation AQUA KEEP 1 OSH-NF, particles having an average particle size of from 200 µm to 300 µm available under the trade designation AQUA KEEP 10SH-P, particles having an average particle size of from 320 µm to 370 µm available under the trade designation AQUA KEEP SA605, particles having an average particle size of from 350 µm to 390 µm available under the trade designations AQUA KEEP SA60SX, SA55SX π and SA 60SL II, and particles having an average particle size of from 250 µm to 350 µm available under the trade designation AQUA KEEP SA60N TYPE II from Sumitomo Seika Chemicals Col, Ltd. (Japan). Also available super absorbent materials are Luquasorb 1010 and Luquasorb 1030 from BASF, Ludwigshafen, Germany.

Thus in summary, the absorbent(s) utilized in the adhesive compositions of the present subject matter is typically one or more agents selected from (i) insoluble swellable polymers, (ii) hydratable polymers, (iii) water soluble polymers, (iv) synthetic absorbents, (v) super absorbent polymers, and/or (vi) combinations of any one or more of (i)-(v).

For certain embodiments, it is useful to utilize one or more types or grades of carboxymethyl cellulose (CMC) in the present subject matter compositions and methods. CMC is a cellulose ether comprised of repeating cellobiose units. These are composed of two anhydroglucose units (beta-glucopyranose residues). A parameter used in referring to grades of CMC is the degree of polymerization. This is the number of anhydroglucose units which are joined through 1,4 glucosidic linkages. Each anhydroglucose unit contains three hydroxyl groups. By substituting carboxymethyl groups for some of the hydrogens of the hydroxyl groups, sodium carboxymethyl cellulose is obtained. The average number of hydroxyl groups substituted per anhydroglucose unit is known as the "degree of substitution." If all three hydroxyls are replaced, the maximum theoretical degree of substitution is 3.0 (impossible to practice).

Another parameter used in reference to CMC is average chain length or degree of polymerization. Average chain length (or the degree of polymerization) and the previously noted degree of substitution determine molecular weight of the CMC polymer.

For many embodiments, the CMC utilized in the present subject matter has a degree of substitution of from about 0.2 to about 1.5, and in other embodiments from about 0.7 to about 1.2. In particular embodiments, the degree of substitution of the CMC is from about 0.65 to about 0.90. The molecular weight of CMC is typically within a range of from about 17,000 to about 700,000. The present subject matter includes CMC grades having molecular weights less than 17,000 and greater than 700,000.

In certain versions of the present subject matter, a particularly useful absorbent is sodium carboxymethyl cellulose commercially available from various sources such as from Ashland Chemical under the designation AQUASORB A500. It is also contemplated that instead of, or in addition to, carboxymethyl cellulose; hydroxypropyl cellulose, hydroxypropylmethyl cellulose, and variants thereof can be used in the present subject matter.

Active Agent(s)

Furthermore, a wide array of active agents can be used in the compositions of the present subject matter. Generally, any active, active agent, or combination of actives and/or active agents which are biologically active and which can be incorporated within the adhesive composition in a stable manner or form, can be utilized. It will be understood that the active(s) are optional. In certain versions of the present subject matter, the active agent is soluble in the vehicle and particularly in polyhydric alcohol(s) when such are utilized as vehicles in the compositions. In certain versions of the present subject matter, the active agent forms a complex with the crystallization inhibitor(s), described in greater detail herein which for example can be polyvinylpyrrolidone. The complex typically results from hydrogen bonding between the active(s) and the inhibitor(s).

In certain aspects, the active(s) can be for example the pain relievers or analgesics fentanyl, butorphanol, morphine, buprenorphine, naloxone, codeine, menthol, methyl salicylate, camphor, capsaicin, acetylsalicylic acid; local anaesthetics such as lidocaine, anti-acne drugs like retinoic acid; anti-angina drugs like nitroglycerin, isosorbide dinitrate, nifedipine, nicardipine; antiarrhythmics like timolol; antibacterials like amikacin, cephalosporins, macrolides, tetracyclines, quinolones, nitrofurantoin; anti-convulsives like carbamazepine, phenobarbital, nitrazepam; antidepressants like tricyclics, bupropion, sertraline, pergolide, fluoxetine; anti-rheumatics like diclofenac, ibuprofen, piroxicam, ketoprofen, thiocolchicoside, methotrexate; sex hormones like progesterone, testosterone, estradiol, levonorgestrel; antifungals like clotrimazole, ketoconazole, miconazole; antihypertensives like sotalol, alprenolol, captopril, enalapril, felodipine, nicardipine, reserpine; anti-hypothyroid drugs like thyroxine; anti-malarials like artemesine, cinchonidine, primaquine; anti-migraine drugs like ergotamine, sumatriptan, rizatriptan; anti-nausea drugs like domperidone, chlorpromazine, methoclopramide, scopolamine, tetrahydrocannabinoids; skin lighteners like hydroquinone, hydroquinine; dopamine receptor antagonists like pergolide, bromocriptine; muscle relaxants like thiocolchicoside, diazepam; sclerosing agents like ethanolamine, sodium ricinoleate; vitamins like A, B, C, E and precursors or various agents like oxybutynin, finasteride, erythropoetine. Combinations of one or more of these actives are also contemplated including combinations of these agents with still other ingredients.

Crystallization Inhibitors

The present subject matter utilizes one or more crystallization inhibitors in the compositions. Crystallization inhibitors are used to enhance the solubility and stability of the actives in the compositions. Crystallization inhibitors provide for higher concentrations/loading of active agents to be dissolved and once dissolved, inhibit the actives from subsequently precipitating out of solution. By use of these strategies, the crystallization inhibitors thereby increase the availability of the actives for application to human skin during transdermal drug delivery. Although not wishing to be bound to any particular theory, it is believed that, because there are more actives available in an amorphous state within the adhesive matrix, the crystallization inhibitors indirectly increase the amount of actives delivered to the skin. High concentrations of dissolved active ingredients in the matrix of transdermal therapeutic systems generally make possible a high flow of active ingredients to and through the skin to aid in treatment.

A wide range of crystallization inhibitors can be incorporated in the present subject matter compositions to enhance the availability of the solvated actives for treatment. For example, the crystallization inhibitor may comprise polyvinylpyrrolidone, polyacrylamides, polyvinyl alcohols, polyacrylic acids, caseins, gelatins, polyamines/polyethyleneimines, polyethylene glycols, cellulose, cellulose derivatives, methylcellulose, hydroxypropyl cellulose, ethyl cellulose, carboxymethylcellulose, non-urethane associated thickeners, quaternary ammonium alginates, xanthan, pectin, guar gum, guar gum derivatives, carrageenan, carboxypolymethylene, agar, polyethoxylated sorbitols, butyl methacrylate, butyl methacrylate derivatives, 2-dimethylaminoethyl methacrylate, methyl methacrylate, polyaminoamides, polyaminoimidazolines, polyetherurethaneamines, polyethylene oxide, polyacrylic acid, silica, silicon dioxide, starch, starch derivatives, dextrin, cyclodextrins, dextran, rosin esters, sterols, bile acids, polyglucosamines, monoacylglycerols, glycerol monooleate, glycerol monolinoleate, glycerol monopalmitate, glycerol monostearate, glycerol monolaurate, glycerol monocaprylate, glycerol monocaprate, and combinations or mixtures thereof.

In certain versions of the present subject matter, the crystallization inhibitor includes polyvinylpyrrolidone (PVP), either alone or in combination with other crystallization inhibitors. PVP is a white, hygroscopic polymer with a weak characteristic odor. PVP is usually in powder form, although it can be in solution, and comprises the monomer N-vinylpyrrolidone as the base unit. By selecting suitable polymerization conditions, a wide range of molecular weights can be obtained, extending from low values of a few thousand daltons to approximately 2.2 million daltons, i.e. 2,200 kDa.

PVP can be either a homopolymer or copolymer, typically synthesized by free-radical polymerization in water or alcohols with a suitable initiator of vinylpyrrolidone (also referred to as N-vinylpyrrolidone, N-vinyl-2-pyrrolidone and N-vinyl-2-pyrrolidinone) as a monomeric unit. PVP polymers include soluble and insoluble homopolymeric PVPs, and copolymers such as vinylpyrrolidone/vinyl acetate and vinylpyrrolidone/dimethylamino-ethylmethacrylate. Substantially cross-linked homopolymers of PVP are insoluble and are generally known in the pharmaceutical industry under the designations polyvinylpolypyrrolidone, crospovidone and PVP. The copolymer vinylpyrrolidone-vinyl acetate is generally known in the pharmaceutical industry under the designations Copolyvidon(e), Copolyvidonum or VP-VAc.

In certain aspects of the present subject matter, the PVP is soluble. The term "soluble" when used with reference to PVP means that the polymer is soluble in water and generally is not substantially cross-linked, and has a weight average molecular weight of less than about 2,200,000. In contrast to most polymers, soluble PVP is readily soluble in water and also in a large number of organic solvents, such as alcohols, amines, acids, chlorinated hydrocarbons, amides and lactams. Soluble PVP polymers have been identified in the pharmaceutical industry under a variety of names, the most commonly used include Povidone, Polyvidon(e), Polyvidonum, Polyvidonum, poly(N-vinyl-2-pyrrolidinone, poly(N-vinylbutyrolactam), poly(l-vinyl-2-pyrrolidone), poly[1-(2-oxo-1-pyrrolidinyl)ethylene]. PVP homopolymer is generally insoluble in the common esters, ethers, hydrocarbons and ketones. When dry, soluble PVP homopolymer is a light flaky powder, which absorbs up to 40% of its weight in water.

The amount and type of PVP required in the embodiments typically depends on the quantity and type of drug present in the adhesive composition, as well as the type of adhesives. Typically, the PVP is present in an amount from about 0.01% to about 30% by weight of the weight of the total adhesive composition. The soluble PVP for certain versions of the present subject matter has a weight average molecular weight of less than about 2,200 kilodaltons (kDa), more particularly less than about 100 kDa, and most particularly less than 54 kDa. In certain versions, it is useful to employ PVP having a weight average molecular weight from about 2,000 to 2,200,000 (i.e. 2 kDa to 2,200 kDa), more particularly from 5,000 to 100,000 (i.e. 5 kDa to 100 kDa), and most particularly 7,000 to 54,000 (i.e. 7 kDa to 54 kDa). In certain versions of the present subject matter it is useful to employ PVP having certain characteristics and/or properties. For example, in certain embodiments, the PVP has a weight average molecular weight (Mw) of from about 9 to about 850 kilodaltons (kDa), and a number average molecular weight (Mn) of from about 2 to about 200 kDa. In certain aspects, the PVP has a glass transition temperature of from about 110° C. to about 180° C. And, in certain embodiments, the PVP has a K-value of from about 15 to about 82. It is also contemplated to utilize PVP exhibiting all of these characteristics.

In certain versions of the present subject matter, it is advantageous to utilize one or more commercially available grades of PVP, such as those under the trade name LUVITEC®, LUVICROSS®, KOLLIDON®, and COLLACRAL®VAL from BASF Corporation; and PLASDONE, POLYPLASDONE and COPOLYMER 958 by ISP Technologies, Wayne, N.J.

BASF offers a wide range of suitable soluble vinylpyrrolidone homopolymers with different molecular weights (K-values) under the name LUVITEC® K. The products are available as a powder or as aqueous solutions. Characteristic parameters of all LUVITEC® K grades are listed in Table 2.

TABLE 2

Representative Grades of PVP

| | K-value: Mw in kDa | Solids content in % | pH-value (10% solution) | Residual NVP content in ppm | Brookfield-RVT Viscosity in mPa · s at 23° C. |
|---|---|---|---|---|---|
| LUVITEC ® K 17 powder | 15-19 | 95.0-100.0 | 3.0-7.0 | ≤100 | 80-180 (40/2/100) |
| LUVITEC ® K 30 powder | 27-33 | 95.0-100.0 | 3.0-7.0 | ≤100 | 80-140 (30/1/50) |
| LUVITEC ® K 80 powder | 74-82 | 95.0-100.0 | 5.0-8.0 | ≤100 | 2500-7000 (20/6/100) |
| LUVITEC ® K 85 powder | 84-88 | 95.0-100.0 | 5.0-9.0 | ≤100 | 5000-20000 (20/6/50) |
| LUVITEC ® K 90 powder | 88-92 | 95.0-100.0 | 5.0-9.0 | ≤100 | 10000-25000 (20/7/100) |
| LUVITEC ® K 90 HM powder | 92-96 | 95.0-100.0 | 5.0-9.0 | ≤100 | 15000-30000 (20/7/100) |
| LUVITEC ® K 30 solution approx. 30% | 27-33 | 29.0-31.0 | 4.0-8.0 | ≤100 | 80-140 (30/1/50) |
| LUVITEC ® K 60 solution approx. 35% | 52-62 | 34.0-36.0 | 7.0-9.0 | ≤300 | 2000-20000 (35/6/50) |

TABLE 2-continued

Representative Grades of PVP

|  | K-value: Mw in kDa | Solids content in % | pH-value (10% solution) | Residual NVP content in ppm | Brookfield-RVT Viscosity in mPa · s at 23° C. |
|---|---|---|---|---|---|
| LUVITEC ® K 85 CQ solution approx. 20% | 83-88 | 19.0-21.0 | 7.0-9.0 | ≤100 | 5000-15000 (20/6/50) |
| LUVITEC ® K 90 CQ solution approx. 10% | 90-98 | 9.5-10.5 | 7.0-9.0 | ≤50 | 300-1500 (10/4/100) |
| LUVITEC ® K 90 solution approx. 20% | 90-98 | 19.0-21.0 | 7.0-9.0 | ≤100 | 10000-40000 (20/7/100) |
| LUVITEC ® K 115 CQ solution approx. 10% | 114-130 | 10.5-11.5 | 7.0-9.0 | ≤50 | 2000-5000 (11/6/100) |

Table 3 set forth below presents typical properties of various grades of PVP commercially available under the LUVITEC® trade name.

TABLE 3

Typical Properties of PVP

| LUVITEC ® | K 17 | K 30 | K 60 | K 80 | K 85 | K 90 | K 90 HM | K 115 |
|---|---|---|---|---|---|---|---|---|
| Molecular weight (GPC): | | | | | | | | |
| Mw in kDa | 9 | 50 | 450 | 850 | 1100 | 1400 | 1800 | 2200 |
| Mn in kDa | 2 | 14 | 140 | 200 | 250 | 325 | 375 | 400 |
| Ash content in % | | | | ≤0.02 | | | | |
| Rel. Viscosity (1% in water, 23° C. capillary viscometer) | 1.09 (5%: 1.53) | 1.25 | 1.93 | 3.09 | 3.74 | 5.09 | 5.69 | 12.1 (0.1%: 1.33) |
| Glass transition temperature in ° C. (DSC) | 110 | 175 | 175 | 180 | 180 | 180 | 180 | 180 |
| Particle size in μm (Sympatec-Helos Rodos) | | | | | | | | |
| $X_{10}$ % | 15 | 25 | Only available as solution | 60 | 90 | 90 | 90 | Only available as solution |
| $X_{50}$ % | 25 | 75 | | 160 | 180 | 180 | 180 | |
| $X_{90}$ % | 100 | 130 | | 320 | 350 | 350 | 350 | |
| Color (10% solution, according to Europ. Pharmacopoeia) | Brighter than BY5/B5/R6 | | | | | | | |
| Moisture absorption at saturation in % | 20 (50% rel. humidity, 23° C.) 40 (75% rel. humidity, 23° C.) | | | | | | | |

In certain versions of the present subject matter, the soluble PVP homopolymer used in the present subject matter is a low molecular weight PVP (for example having a molecular weight less than about 60 kDa) that can be used either alone or in combination with other soluble PVP homopolymers or with other crystallization inhibitors. In one aspect the soluble PVP homopolymer used has a molecular weight from about 0.1 kDa to about 54 kDa, more particularly from about 8 kDa to about 10 kDa).

Vehicle(s)

A wide array of vehicles, carriers, and/or solvents can be utilized in the present subject matter compositions. Generally, one or more alcohols (including polyhydric alcohols), terpenes, terpenoids, essential oils, pyrrolidones, fatty acids and their esters, sulfoxides, glycols, and glycerides, phospholipids, lipid synthesis inhibitors, cyclodextrin complexes, amino acid derivatives, clofibric acid, dodecyl-N,N-Dimethylamino Acetate (DDAA), enzymes, and combinations thereof can be used as a vehicle for the active agent.

In one aspect, polyhydric alcohols are utilized in the present subject matter compositions. Suitable examples of polyhydric alcohols include dihydric alcohols, such as ethylene glycol, propylene glycol, 1,3- and 1,4-butanediols, 1,6-hexanediol, methylene oxidepentyl glycol, diethylene glycol, bis(hydroxymethyl)cyclohexane, bis(hydroxyethyl) benzene, hydrogenated bisphenol A, hydrogenated bisphenol F, polyethylene glycols, polytetramethylene glycols, polyester diols and silanol-terminated polysiloxanes; trihydric alcohols, such as glycerol, trimethylol propane, trimethylol ethane, 1,2,3-butane triol, 1,2,6-hexane triol and polyester triols; and polyhydric alcohols having 4 to 8 or more hydroxyl groups, such as pentaerythritol, diglycerol, α-methylglucoside, sorbitol, xylitol, mannitol, volemitol, erythritol, threitol, glucose, fructose, sucrose, and the like.

Other suitable vehicles, for example, are monovalent and multivalent alcohols with up to 24 carbon atoms, such as 1,2-propanediol, 1,3-propanediol, 1,2-ethanediol, glycerol or lauryl alcohol; free carboxylic acids with up to 24 carbon atoms, such as lauric acid; fatty acid esters with up to 24 carbon atoms in the fatty acid component and up to 20 carbon atoms in the monovalent or multivalent alcohol component, such as isopropyl myristate, glycerol monopalmitate, dodecanoyl acetate; terpenes, amides, urea and mixtures of these penetration enhancers. However, it will be appreciated that the present subject matter includes the use of other vehicles, carriers, and/or solvents instead of, or in addition to those mentioned herein.

Additional Aspects

In certain embodiments, the adhesive composition is a hydrocolloid adhesive. A base hydrocolloid adhesive formulation generally comprises a hot melt adhesive blended with an absorbent such as sodium carboxymethylcellulose (CMC), gelatin, pectin, alginate, polyacrylate superabsorbent, or the like. Other hydrocarbon resins, such as polyisobutylene, can also be included to adjust adhesive properties. Any of these formulations can be selected for the base adhesive in a drug-delivery application in accordance with the present subject matter.

For effective drug delivery it is advantageous to incorporate a polyhydric alcohol which acts primarily as a vehicle into which the drug is actually dissolved, but may also serve a secondary function as a skin penetration enhancer. Propylene glycol is an example of a polyhydric alcohol which serves both purposes. Other examples of polyhydric alcohol vehicles include glycerol and polyethylene glycols, typically with molecular weights between 200 and 1,000 Da, or any mixtures thereof.

It is further advantageous in certain applications, to include a particular crystallization inhibitor to stabilize the drug or active agent(s). One particular crystallization inhibitor is polyvinylpyrrolidone (PVP), which generally includes soluble PVP homopolymers of low molecular weight. Such low molecular weight PVP is incorporated in the present subject matter compositions in accordance with the present subject matter. Typically formulations not including PVP, are limited in two ways: 1) there is a limit to the amount of active agent that can be dissolved within the vehicle, and 2) there is a limit to the amount of active agent/vehicle that can be introduced into the adhesive matrix. In the first instance, super-saturation of the active agent in the vehicle may lead to undesirable nucleation and growth of crystals, especially over time. In the second instance, vehicles incompatible with the adhesive matrix can migrate to the adhesive surface and reduce the tack or bonding strength of the adhesive, thus leading to unpredictable release kinetics for the active agent. Although the present subject matter includes the use of a wide array of agents besides PVP as crystallization inhibitors, for many applications PVP are useful as crystallization inhibitors.

The advantages of using PVP to increase the percentage of active agent in an adhesive composition include the following. In one aspect, PVP inhibits the crystallization of an active agent in the vehicle, thus allowing a higher loading of active agent within the vehicle. In a second aspect, PVP increases the viscosity of the active agent/vehicle phase, and in some cases creates a gel or pseudo-gel, which can prevent the active agent/vehicle phase from migrating to the surface of the adhesive matrix after dispersion therein. The adhesive composition is thus stabilized, allowing for higher loading of the active agent/vehicle phase within the adhesive matrix.

In certain versions, the present subject matter adhesive compositions provide for a combination of i) an adhesive forming a continuous phase, ii) an absorbent forming a first discontinuous phase dispersed in the continuous phase, and iii) an active agent and PVP dissolved or distributed in a vehicle forming a second discontinuous phase dispersed in the continuous phase. Once blended together, these ingredients form a complex multi-phase system in which the various components i), ii), and iii) typically form separate domains but are nevertheless homogeneously blended into a single cohesive mass. The multi-phase adhesive composition maintains effective adhesive properties. It will also be understood that the present subject matter is not limited to multi-phase compositions. Instead, the subject matter includes single or unitary phase compositions or systems.

In view of these aspects, the present subject matter provides a hydrocolloid adhesive formulation as set forth below in Table 4. The active agent may for example be ibuprofen.

TABLE 4

Representative Adhesive Compositions

| Weight Percentage | Component |
| --- | --- |
| 30% to 80% | i) Hot Melt Adhesive |
| 0.5% to 45% | ii) Absorbent |
| 0.5% to 10% | iii) Active Agent(s) |
| 0.5% to 20% | iii) Polyvinylpyrrolidone (PVP), (Crystallization Inhibitor) |
| 0.5% to 20% | iii) Polyhydric Alcohol (Vehicle) |

In one embodiment, the adhesive composition comprises components in a particular weight ratio of about 102 parts adhesive, about 41 parts absorbent, about 9 parts vehicle, about 9 parts active agent, and about 3 parts crystallization inhibitor. Without the absorbent, the combination of 102 parts adhesive, about 9 parts vehicle, about 9 parts active agent, and about 3 parts crystallization inhibitor produces a non-tacky gel-like mixture not suitable for use as an adhesive for delivering an active agent to biological skin. In this embodiment, the particular addition of the absorbent provides a tacky composition that otherwise, is not tacky.

In another embodiment, the weight ratio of crystallization inhibitor to the vehicle ranges from about 0.1% (i.e. 1:10) to about 100% (i.e. 1:1), or more. In other aspects, the weight ratio of the noted components is from about 0.1% (i.e. 1:10) to about 75% (i.e. 3:4) or from about 0.1% (i.e. 1:10) to about 50% (i.e. 1:2). In certain versions, the weight ratio of crystallization inhibitor to vehicle is from about 0.1% to about 300%. As the ratio in a particular adhesive composition increases, i.e., when the amount of crystallization inhibitor approaches the amount of the vehicle, then the solubility of the active agent in the vehicle increases, allowing for higher loading of the active agent in the vehicle.

In certain embodiments, the hot melt adhesive includes styrene-isoprene copolymers, the polyhydric alcohol is propylene glycol, the PVP is a soluble homopolymer with molecular weight less than about 60 kDa, and the absorbent is sodium carboxymethylcellulose (CMC).

Notably, these mixtures can be processed, i.e. blended and extruded, at temperatures less than 100° C. and in certain versions less than 75° C., which is the critical thermal breakdown temperature for many actives, such as ibuprofen for example. This is a unique feature that cannot be achieved with solvent-based acrylic adhesives because of the high drying temperatures that such adhesives typically require.

PVP enhances the solubility of certain actives such as ibuprofen in a propylene glycol vehicle, as shown in FIG. 1. Without PVP present, the room-temperature saturation concentration is 17.3 wt % ibuprofen in propylene glycol. The solubility of ibuprofen increases to 27.7 wt % when the vehicle includes PVP to obtain a mixture of 75% propylene glycol, 25% PVP (BASF LUVITEC K17, typical Mw of about 9,000 Da). The enhanced solubility enables increased loading of the drug without the risk of crystallization.

Figure 2:
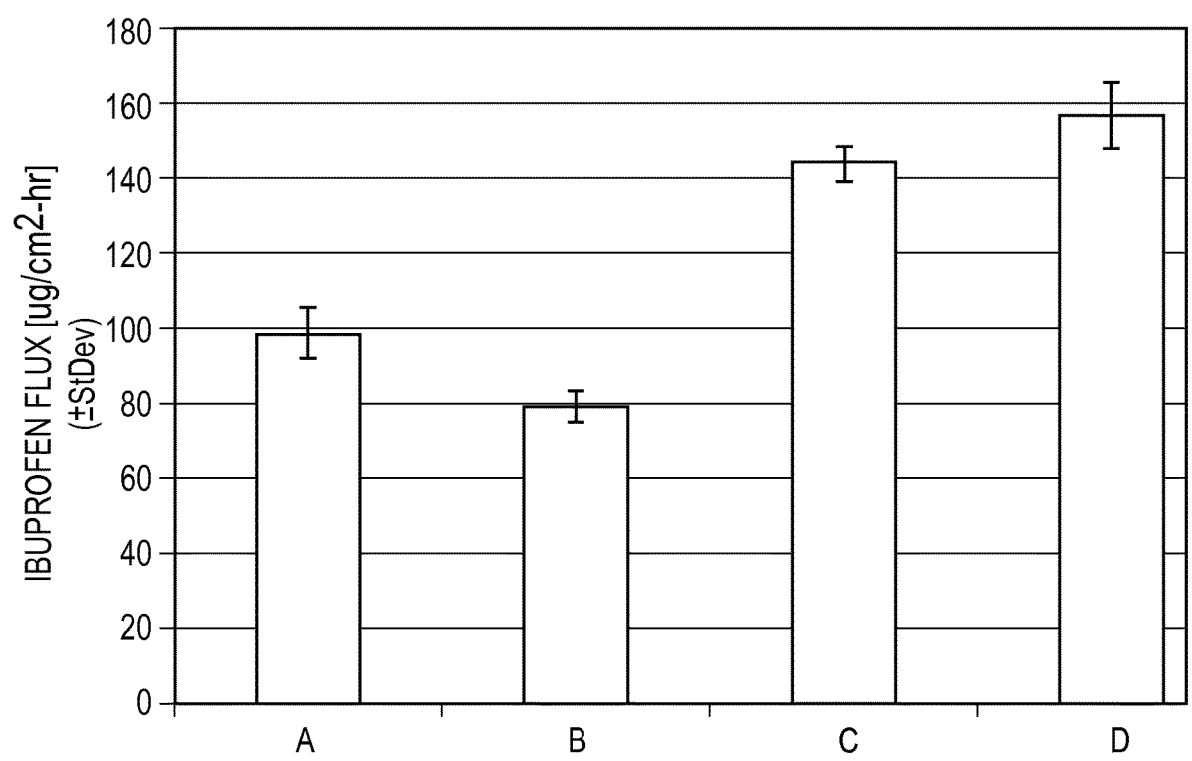
FIG. 2 is a graph of flux of an active agent from various compositions described in greater detail herein, several of which are in accordance with the present subject matter.

The mixture of propylene glycol with PVP also enhances the release kinetics of ibuprofen, as shown in FIG. 2. Compared to a mixture of ibuprofen with hot melt adhesive alone, or to a mixture of ibuprofen with hot melt adhesive and absorbent; mixtures incorporating PVP/propylene glycol blends have approximately 50% higher release rates. Specifically, FIG. 2 illustrates flux of ibuprofen released from various adhesive formulations measured using Franz diffusion cells employing a silicone rate-limiting membrane and 40% ethanol/saline as the receptor solution. In FIG. 2, composition A is 5% ibuprofen in hot melt adhesive. Composition B is 5% ibuprofen in hot melt adhesive containing CMC. Composition C is 5% ibuprofen in hot melt adhesive containing CMC and a mixture of 17% PVP in propylene glycol. And, composition D is 5% ibuprofen in hot melt adhesive containing CMC and a mixture of 43% PVP in propylene glycol. Compositions C and D represent embodiments of the present subject matter.

Formulations containing PVP are more stable in terms of ibuprofen crystallization when compared to non-PVP-containing counterparts. Differential scanning calorimetry of a 5% ibuprofen formulation containing 10% propylene glycol and 34% CMC reveals a thermal transition that is absent in an equivalent formulation containing PVP. The transition is attributed to the melting of crystals contained with this material that are absent in materials containing PVP.

In accordance with the present subject matter, the use of a combination of absorbents and crystallization inhibitors provides unexpected advantages which include significantly improved adhesive properties. Drug release may also be enhanced by the inclusion of an absorbent material. Stability of the active(s) is also promoted by use of the crystallization inhibitors.

Another particular advantage of the present subject matter compositions, is that the compositions can be processed at low temperatures. This is particularly important for a drug such as ibuprofen, which degrades at 75° C. In certain versions of the present subject matter, compositions can be processed at 65-70° C. For a solvent-based system, for example, the resulting composition would need to be processed at much higher temperatures in order to dry it or remove vehicle or solvent. Similarly, rubber hot melts would be processed at something more like 150° C.

In certain embodiments, the adhesive compositions of the present subject matter exhibit particular Peel on polyethylene values and/or particular Tack values. The measurement of these properties is described in greater detail herein in conjunction with various evaluations described herein. In certain versions, the adhesive compositions which comprise a combination of absorbent and crystallization inhibitor, exhibit a Peel on polyethylene value of at least 0.5 N/in, and more particularly at least 1.5 N/in, and more particularly at least 2.5 N/in. In certain versions, the adhesive compositions exhibit a Tack value of at least 10 N/in, more particularly at least 25 N/in, and more particularly at least 40 N/in. In certain aspects of the present subject matter, the compositions which include a combination of absorbents and crystallization inhibitors exhibit both of the noted Peel and Tack values.

In addition to exhibiting the previously noted properties, in particular embodiments of the present subject matter, the adhesive compositions also exhibit a relatively high fluid handling characteristic or ability. The characteristic of relatively high fluid handling ability is exhibited in one or more fashions as follows.

In one aspect, the relatively high fluid handling ability of the present subject matter adhesive compositions is indicated by the compositions exhibiting a static absorption of at least about 50 $g/m^2/24$ hours. In certain versions of the present subject matter, the adhesive compositions exhibit a static absorption of at least 100 $g/m^2/24$ hours; of at least 500 $g/m^2/24$ hours; of at least 1,000 $g/m^2/24$ hours; of at least 2,500 $g/m^2/24$ hours; and in certain embodiments at least 5,000 $g/m^2/24$ hours. More particularly, certain adhesive embodiments exhibit a static absorption of 5,000 to 10,000 $g/m^2/24$ hours.

In another aspect, the relatively high fluid handling characteristics of the adhesive compositions is indicated by its moisture vapor transmission rate (MVTR). Generally, the MVTR of the present subject matter adhesive compositions is at least 25 $g/m^2/24$ hours. In certain embodiments of the present subject matter, the adhesive compositions exhibit MVTR values of at least 50 $g/m^2/24$ hours; at least 100 $g/m^2/24$ hours; at least $200/g/m^2/24$ hours; at least 350 $g/m^2/24$ hours; and in certain versions, greater than 500 $g/m^2/24$ hours. More particularly, certain adhesive embodiments exhibit MVTR values of 500 to 1000 $g/m^2/24$ hours.

In certain versions of the present subject matter, the adhesive compositions exhibit a static absorption of at least 500 $g/m^2/24$ hours and an MVTR value of at least 25 $g/m^2/24$ hours. A description of determining static absorption and MVTR is provided herein.

Methods

The present subject matter also provides various methods. In one version, a method of enhancing the adhesive properties of an adhesive composition used for delivering an active agent to biological skin is provided. The adhesive composition comprises an adhesive, a vehicle, an active agent, and one or more absorbents. The method further includes dispersing one or more crystallization inhibitors in the adhesive composition. The adhesive, absorbent(s), active agent(s), vehicle, and crystallization inhibitor(s) are as described herein. The various components can be incorporated with one another, blended, and/or otherwise combined in techniques or operations known in the art.

The present subject matter also provides a method of delivering an active agent to biological skin. The method comprises providing an article defining at least one face. The method also comprises depositing an adhesive composition on the face of the article. The adhesive composition includes an adhesive in a weight concentration of from about 30 wt % to about 80 wt %, an absorbent in a weight concentration of from about 0.5 wt % to about 45 wt %, a vehicle in a weight concentration of from about 0.5 wt % to about 20 wt %, an active agent in a weight concentration of from about 0.5 wt % to about 10 wt %, and a crystallization inhibitor in a weight concentration of from about 0.5 wt % to about 20 wt %. These percentages are all based upon the weight of the adhesive composition. The method further comprises applying the article to the skin, whereby the adhesive composition contacts the skin and the active agent is delivered to the skin. The active agent(s) is thereby released from the adhesive composition and is transferred to a wound or other region on biological skin. The components of the adhesive composition are as described herein.

Medical Articles

The adhesive compositions described herein can be used in association with a wide array of medical articles. Non-limiting examples of such articles include wound dressings, surgical dressings, medical tapes, athletic tapes, surgical tapes, sensors, electrodes, ostomy appliances or related components such as sealing rings, catheters, connector fittings, catheter hubs, catheter adapters, fluid delivery tubes, electrical wires and cables, negative pressure wound therapy (NPWT) components, surgical drains, wound draining components, IV site dressings, prostheses, stoma pouches, buccal patches, transdermal patches, dentures, hairpieces, bandages, diapers, medical padding for example liposuction padding, hygiene pads, corn and callous pads, pads for cushioning and protecting blisters, toe cushioning pads, and pads for protecting and cushioning tube sites such as tracheotomy tubes. The medical articles include one or more regions or surfaces to which the adhesive compositions of the present subject matter are applied. Forming a layer, coating, or other region of adhesive on an article enables the article to be adhered to a wide range of surfaces, including skin. It will be understood that the present subject matter is not limited to any of these articles. Instead, the subject matter includes the use of the adhesive compositions with other articles besides those noted herein. The medical articles may also include one or more layers covering the adhesive layer or coating such as a release liner.

EXAMPLES

Evaluations were undertaken to assess several adhesive compositions in accordance with the present subject matter. The materials used in the adhesive compositions were as follows:
- Adhesive: T2650 (Avery Dennison), styrene-isoprene hot melt adhesive;
- Absorbent: AQUASORB A500 (Ashland), sodium carboxymethyl cellulose;
- PVP: LUVITEC K17 (BASF), soluble PVP homopolymer with average molecular weight of 9 kDa;
- Drug: Ibuprofen (BASF), USP-grade;
- Vehicle: propylene glycol.

Various compositions were prepared. For each composition, a comparative composition was prepared.

For each resulting set of compositions, the following measurements were made: (i) adhesion to polyethylene, i.e. "Peel", (ii) tack, (iii) release of active after 2 hours, i.e. "Elution 2 hr", (iv) release of active after 6 hours, i.e. "Elution 6 hr", and (v) fluid handling capacity, i.e. "FHC".

Specifically, samples were prepared and evaluated as follows.

Sample Preparation

Adhesive components were blended together in a sigma-blade mixer heated to approximately 70° C. After blending, all adhesive specimens were pressed into sheets approximately 0.8 mm thick and laminated on one side to an adhesive-coated polyurethane film, 70 microns in thickness.

Peel

Specimens measuring one inch wide by approximately five inches long were applied to the surface of a polyethylene film using a 4.5 lb roller and allowed to dwell for approximately one minute before peeling off at a ninety degree angle and a rate of 12 inches/minute using a tensile tester to record the average force required for removal.

Tack

Specimens were mounted to a fixture, adhesive side up. A piece of 5 mil polyester film measuring 15 cm long by 2.54 cm wide was formed into a loop and brought into contact with the adhesive surface, making a 1 inch×1 inch contact area. Then the polyester loop was pulled away from the adhesive. A tensile tester was used to contact and pull the loop away from the adhesive at a crosshead speed of 12 inches/min, and the peak force measured during removal was taken as the quantitative measurement of tack.

Elution

A disk was cut from each specimen measuring 0.75 inches in diameter and placed in a vial containing approximately 20 mL of a solution of ethanol and saline (40% ethanol by volume in a solution of 0.9% sodium chloride in water by weight). The vial was tumbled in ambient temperature conditions, and after two and six hours samples of the solution were taken out for analysis. The concentration of ibuprofen in the solution was quantified using ultraviolet absorbance allowing the amount of ibuprofen release to be calculated as a percentage by weight of the total amount present in the sample.

Fluid Handling Capacity

Fluid Handling Capacity is a measure of the combined ability of the composite to take up moisture and to evaporate it to the environment. This test is performed by laminating a sample cut to the size of a Paddington cup to the cup on the side having the rubber ring. The circular sealing ring is placed on the sample of the cup and the screws are secured. The cup is weighed (W1). The cup is then turned upside down and filled with 20 ml of a saline solution (0.9% wt NaCl and 0.04% wt $CaCl_2$ in deionized water). The metal sealing place is secured to the top side of the cup. The filled cup is weighed (W2). The cup is placed sample side down into an oven at 37° C. for 24 hours. After 24 hours, the cup is removed from the oven and allowed to cool to room temperature for 30 minutes. The cup is then weighed (W3). The metal sealing plate is removed and the cup is emptied. The cup is allowed to stand for 15 minutes on a tissue to remove the saline solution, and then weighed (W4). The test conditions are 23° C.)(±2° and 50% (±2%) relative humidity. The samples tested herein had a thickness of 0.8 mm. The Moisture Vapor Transmission Rate (MVTR) equals (W2−W3)×1000. The Static Absorption equals (W4−W1)×1000. The Fluid Handling Capacity (FHC) in g/10 $cm^2$/24 hours is determined as follows:

$$FHC=(W2-W3)+(W4-W1)$$

Tables 5, 7, 9, and 11 present various compositions which were evaluated. Tables 6, 8, 10 and 12 present results of evaluations of those compositions. Compositions 1 and 2 both lacking a crystallization inhibitor, and Composition 1 also lacking an absorbent, exhibited moderate to poor adhesive Peel and Tack Values. Comparative Compositions A and B were evaluated to assess the effect of incorporating a crystallization inhibitor in the Compositions 1 and 2.

TABLE 5

| Formulations | Composition 1 Parts [Weight Basis] | Comparative Composition A Parts [Weight Basis] |
| --- | --- | --- |
| Hot Melt Adhesive | 100 | 100 |
| Propylene Glycol | 4.5 | 4.3 |
| Polyvinylpyrrolidone | 0 | 2.7 |
| Ibuprofen | 7.4 | 6.9 |
| Absorbent | 0 | 0 |

TABLE 6

| Results of Testing | Composition 1 | Comparative Composition A |
| --- | --- | --- |
| Peel [N/in] | 0.7 | 0.5 |
| Tack [N/in] | 35 | 40 |
| Elution 2 hr [%] | 15 | 12 |
| Elution 6 hr [%] | 28 | 23 |
| FHC [g/$m^2$-day] | 200 | 200 |

TABLE 7

Formulations

| | Composition 2 Parts [Weight Basis] | Comparative Composition B Parts [Weight Basis] |
|---|---|---|
| Hot Melt Adhesive | 100 | 100 |
| Propylene Glycol | 4.3 | 4.4 |
| Polyvinylpyrrolidone | 0 | 2.9 |
| Ibuprofen | 7.2 | 7.2 |
| Absorbent | 29 | 28 |

TABLE 8

Results of Testing

| | Composition 2 | Comparative Composition B |
|---|---|---|
| Peel [N/in] | 0.0 | 2.8 |
| Tack [N/in] | 10 | 50 |
| Elution 2 hr [%] | 22 | 20 |
| Elution 6 hr [%] | 44 | 35 |
| FHC [g/m$^2$-day] | 7,500 | 6,300 |

Adding polyvinylpyrrolidone (PVP) has a minimal effect on compositions that do not contain absorbent (see Tables 5 and 6). However, adding PVP to an absorbent-containing composition leads to a dramatic increase in Tack and Peel (see Tables 7 and 8). Thus, Comparative Composition B is an example of the present subject matter compositions.

Similarly, Compositions 3 and 4 both lacking a crystallization inhibitor, and Composition 3 also lacking an absorbent, exhibited moderate to poor adhesive Peel and Tack values. Comparative Compositions C and D were evaluated to assess the effect of incorporating a crystallization inhibitor in the Compositions 3 and 4.

TABLE 9

Formulations

| | Composition 3 Parts [Weight Basis] | Comparative Composition C Parts [Weight Basis] |
|---|---|---|
| Hot Melt Adhesive | 100 | 100 |
| Propylene Glycol | 7.0 | 7.3 |
| Polyvinylpyrrolidone | 0 | 9.4 |
| Ibuprofen | 8.3 | 8.7 |
| Absorbent | 0 | 0 |

TABLE 10

Results of Testing

| | Composition 3 | Comparative Composition C |
|---|---|---|
| Peel [N/in] | 0.1 | 0.3 |
| Tack [N/in] | 38 | 42 |
| Elution 2 hr [%] | 15 | 9 |
| Elution 6 hr [%] | 28 | 19 |
| FHC [g/m$^2$-day] | 200 | 300 |

TABLE 11

Formulations

| | Composition 4 Parts [Weight Basis] | Comparative Composition D Parts [Weight Basis] |
|---|---|---|
| Hot Melt Adhesive | 100 | 100 |
| Propylene Glycol | 7.0 | 6.9 |
| Polyvinylpyrrolidone | 0 | 8.9 |
| Ibuprofen | 8.2 | 8.3 |
| Absorbent | 38 | 38 |

TABLE 12

Results of Testing

| | Composition 4 | Comparative Composition D |
|---|---|---|
| Peel [N/in] | 0.0 | 2.6 |
| Tack [N/in] | 8 | 41 |
| Elution 2 hr [%] | 25 | 16 |
| Elution 6 hr [%] | 52 | 31 |
| FHC [g/m$^2$-day] | 8,300 | 8,400 |

Adding polyvinylpyrrolidone (PVP) has a minimal effect on compositions that do not contain absorbent (see Tables 9 and 10). However, adding PVP to an absorbent-containing composition leads to a dramatic increase in Tack and Peel (see Tables 11 and 12). Thus, Comparative Composition D is another example of the present subject matter compositions.

Many other benefits will no doubt become apparent from future application and development of this technology.

All patents, applications, standards, and articles noted herein are hereby incorporated by reference in their entirety.

As described hereinabove, the present subject matter solves many problems associated with previous strategies, systems or devices. However, it will be appreciated that various changes in the details, materials and arrangements of components and operations, which have been herein described and illustrated in order to explain the nature of the subject matter, may be made by those skilled in the art without departing from the principle and scope of the subject matter, as expressed in the appended claims.

What is claimed is:

1. An adhesive composition consisting of:
    at least one adhesive component in an amount in the range of 61.7 to 90 wt %, wherein the adhesive component is a hot melt adhesive that is able to be processed at a temperature below 75° C.;
    at least one vehicle in an amount in the range of 0.1 to 4.3 wt %, wherein the vehicle is a polyhydric alcohol selected from the group consisting of propylene glycol, glycerol, polyethylene glycol, and combinations thereof;
    at least one hydrophilic absorbent in an amount in the range of 0.1 to 23.4 wt %, wherein the hydrophilic absorbent is carboxymethyl cellulose;
    at least one crystallization inhibitor in an amount in the range of 0.1 to 5.5 wt %, wherein the crystallization inhibitor includes polyvinylpyrrolidone;
    optionally at least one tackifier; and
    optionally at least one plasticizer;
    wherein at least one active agent in an amount in the range of 0.5 to 20 wt % is dissolved in the vehicle and the crystallization inhibitor prior to addition to the adhesive component; and wherein the adhesive composition exhibits a Peel on polyethylene value of at least 2.5 N/in and a Tack value of at least 40 N/in.

2. The adhesive composition of claim 1, wherein the active agent is selected from the group consisting of analgesics, local anesthetics, anti-acne agents, anti-angina agents, antiarrhythmics, antibacterial, anti-convulsives, anti-depressants, anti-rheumatics, sex hormones, anti-fungals, anti-hypertensives, anti-hypothyroid agents, anti-malarials, anti-migraine agents, anti-nausea agents, skin lighteners, dopamine receptor antagonists, muscle relaxants, sclerosing agents, vitamins and combinations thereof.

3. The adhesive composition of claim 2, wherein the active agent includes an anti-rheumatic.

4. The adhesive composition of claim 3, wherein the anti-rheumatic is ibuprofen.

5. The adhesive composition of claim 1, wherein the adhesive composition exhibits a static absorption of at least 50 g/m$^2$/24 hours.

6. An article for adhesive attachment to a surface of interest, the article comprising:
a substrate defining at least one face; and
the adhesive composition of claim 1.

7. The article of claim 6 wherein the article is a medical article.

8. The article of claim 7 wherein the medical article is selected from the group consisting of wound dressings, surgical dressings, medical tapes, athletic tapes, surgical tapes, sensors, electrodes, ostomy appliances, sealing rings, catheters, connector fittings, catheter hubs, catheter adapters, fluid delivery tubes, electrical wires and cables, negative pressure wound therapy (NPWT) components, surgical drains, wound draining components, IV site dressings, prostheses, stoma pouches, buccal patches, transdermal patches, dentures, hairpieces, bandages, diapers, medical padding, liposuction padding, hygiene pads, corn and callous pads, blister cushioning and protection pads, toe cushioning pads, pads for protecting and cushioning tube sites, and tracheotomy tubes.

9. The adhesive composition according to claim 1, wherein the at least one crystallization inhibitor is present in an amount in the range of 0.1 to 2.4 wt %.

* * * * *